(12) United States Patent  (10) Patent No.: US 8,172,571 B2
Watson  (45) Date of Patent: May 8, 2012

(54) LIGHT MIRROR

(76) Inventor: Jeffrey A. Watson, Fayetteville, NY (US)

( * ) Notice: Subject to any disclaimer, the term of this patent is extended or adjusted under 35 U.S.C. 154(b) by 1351 days.

(21) Appl. No.: 11/277,464

(22) Filed: Mar. 24, 2006

(65) Prior Publication Data

US 2007/0224571 A1    Sep. 27, 2007

(51) Int. Cl.
*A61C 1/00* (2006.01)
(52) U.S. Cl. .......................................... 433/31
(58) Field of Classification Search ............ 433/30–31, 433/29; 362/109, 135, 138, 800; 600/247, 600/248
See application file for complete search history.

(56) References Cited

U.S. PATENT DOCUMENTS

| | | | |
|---|---|---|---|
| 2,907,110 A | 10/1959 | O'Hara | |
| 3,052,031 A | 9/1962 | Piscitelli | |
| 3,082,762 A | 3/1963 | Gnehm | |
| 3,638,013 A | 1/1972 | Keller | |
| 3,969,824 A | 7/1976 | Widen et al. | |
| 4,279,594 A | 7/1981 | Rigutto | |
| 4,925,391 A | 5/1990 | Berlin | |
| 4,931,015 A | 6/1990 | Amadei | |
| 4,993,945 A | 2/1991 | Kimmelman et al. | |
| 5,139,420 A * | 8/1992 | Walker ............................ | 433/31 |
| 5,139,421 A | 8/1992 | Verderber | |
| 5,286,192 A * | 2/1994 | Dixon ............................. | 433/80 |
| 5,457,611 A | 10/1995 | Verderber | |
| 5,951,284 A | 9/1999 | Lake | |
| 6,106,159 A | 8/2000 | Caplan et al. | |
| 6,200,134 B1 * | 3/2001 | Kovac et al. ................... | 433/29 |
| 6,276,934 B1 * | 8/2001 | Rakocz ......................... | 433/29 |
| 6,443,729 B1 | 9/2002 | Watson | |
| 6,544,036 B1 * | 4/2003 | Brattesani ...................... | 433/30 |
| 6,575,744 B1 | 6/2003 | Oshida | |
| 6,702,577 B2 | 3/2004 | Wong | |
| 6,942,658 B1 * | 9/2005 | Rizoiu et al. .................. | 606/16 |
| 2003/0207229 A1 * | 11/2003 | Wong ............................. | 433/31 |
| 2006/0003284 A1 * | 1/2006 | Sale et al. ...................... | 433/29 |

OTHER PUBLICATIONS

International Search Report, dated Oct. 3, 2007, by the International Bureau.

* cited by examiner

*Primary Examiner* — Heidi M Eide
(74) *Attorney, Agent, or Firm* — Holland & Hart LLP

(57) ABSTRACT

A light mirror includes a mirror attached to a handle. The mirror is arranged at an angle from a longitudinal axis of the handle. A light source inside the handle directs light from a light source through a light waveguide adjacent to the light source. The light waveguide is internally reflective to reflect substantially all of the light from the light waveguide. Optionally, the light mirror includes an annular air flow substantially aligned with a longitudinal axis to cool the handle and the light source as well as keep a reflective surface of the mirror free of debris, water, restorative materials, tooth structure, and aluminum oxide powder.

34 Claims, 11 Drawing Sheets

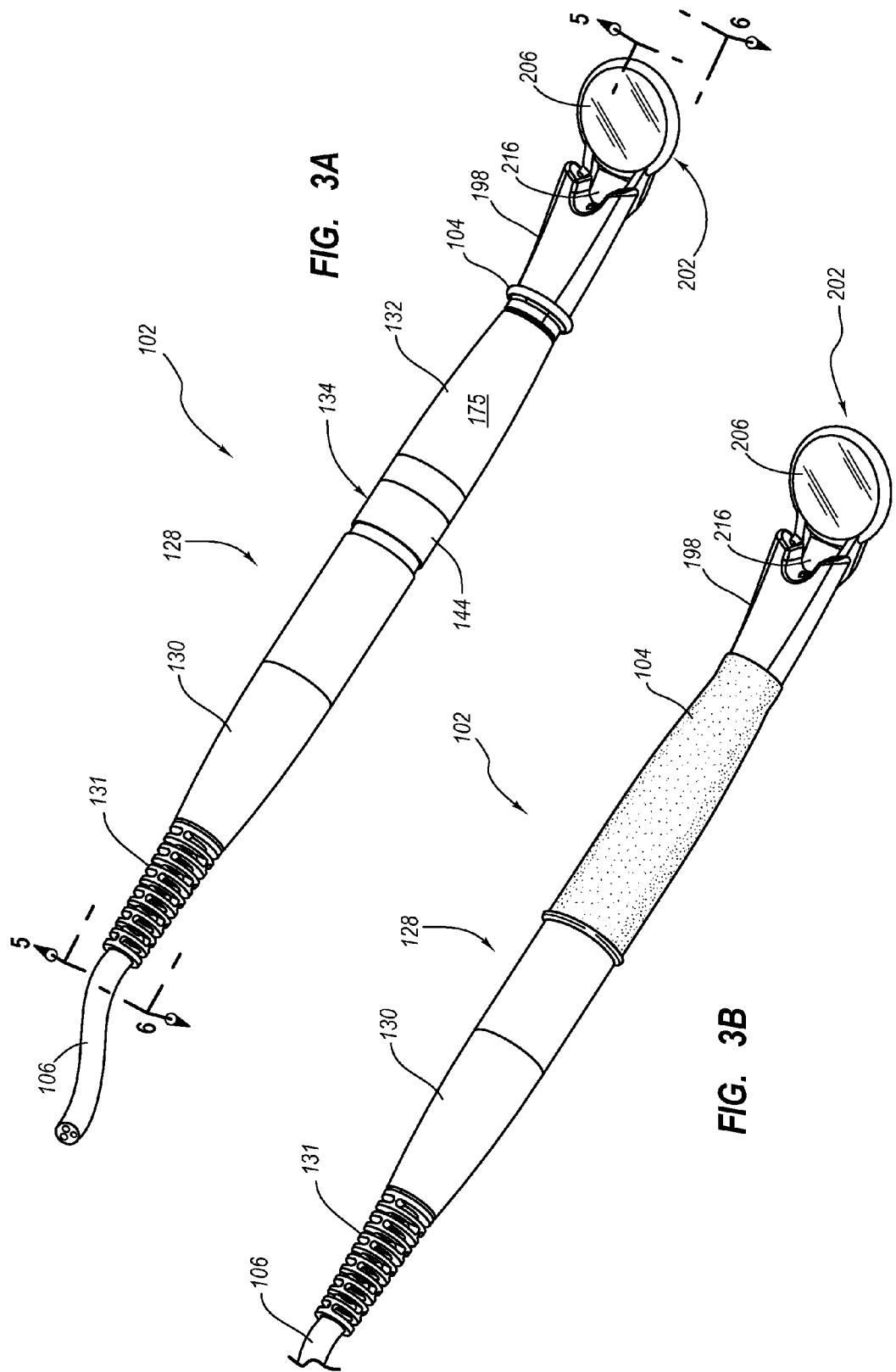

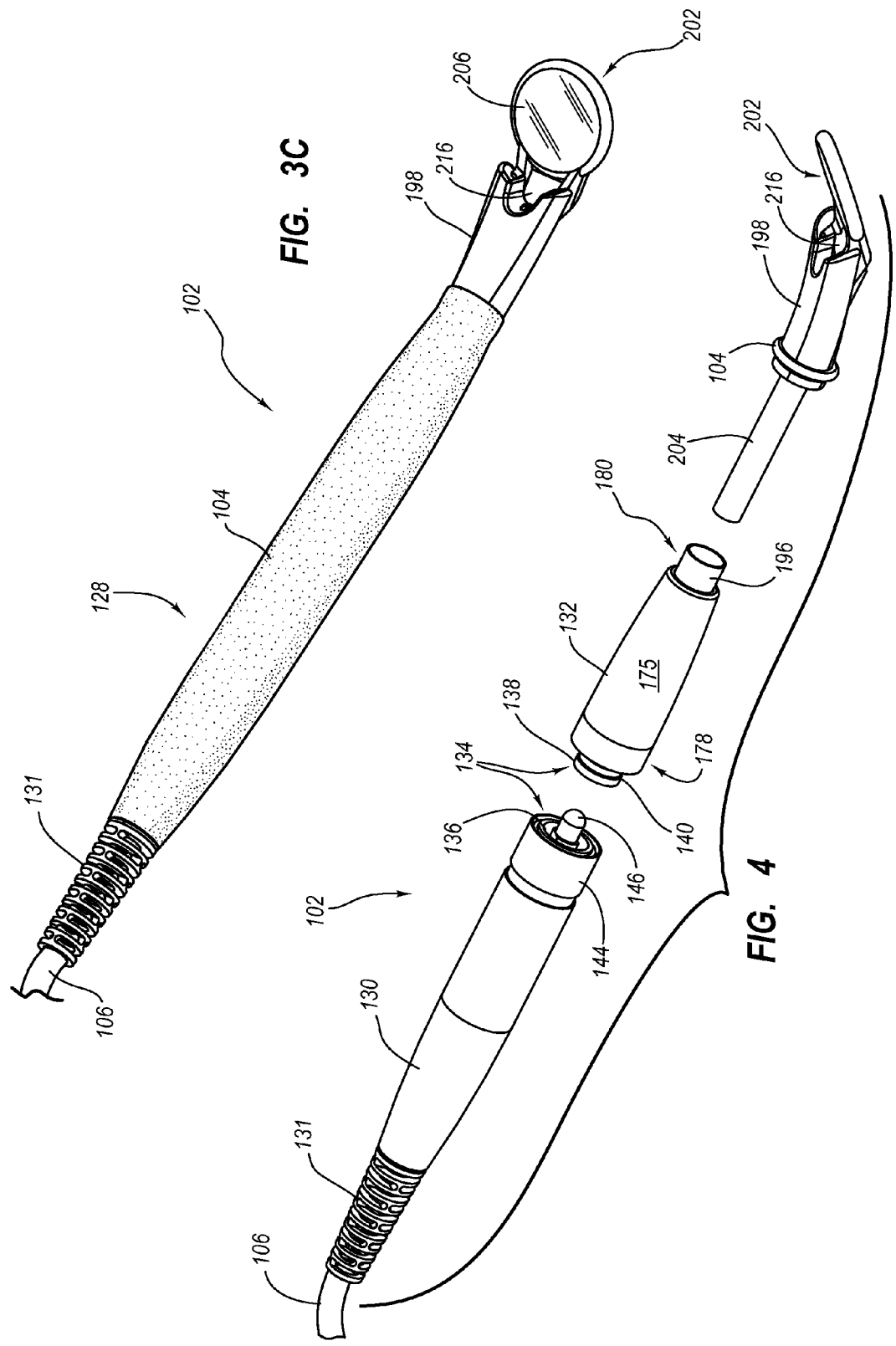

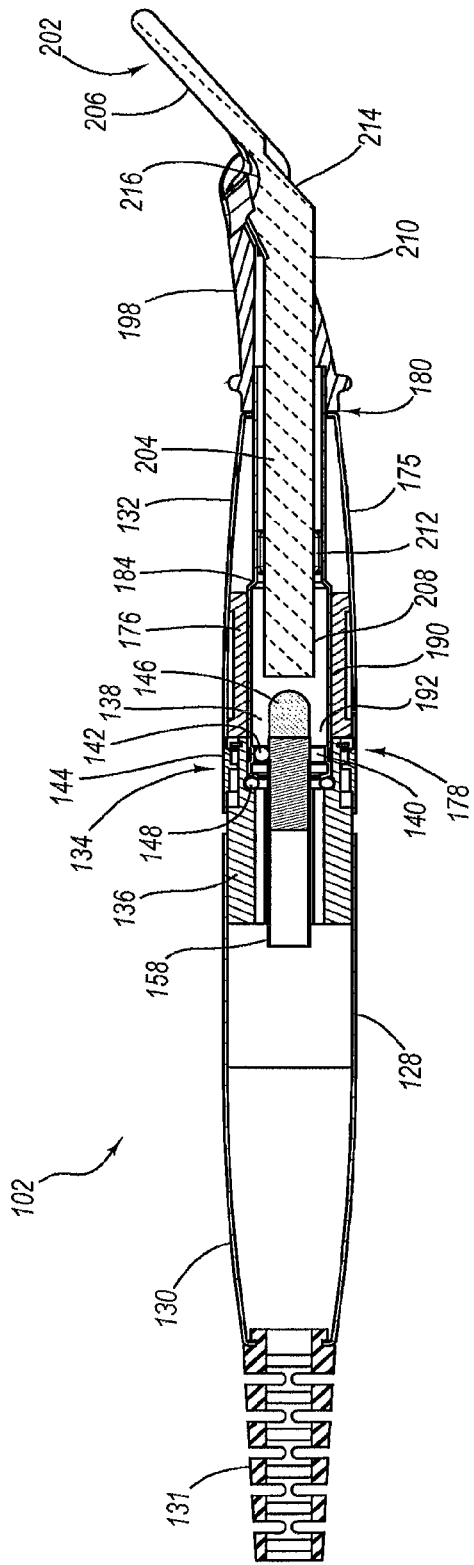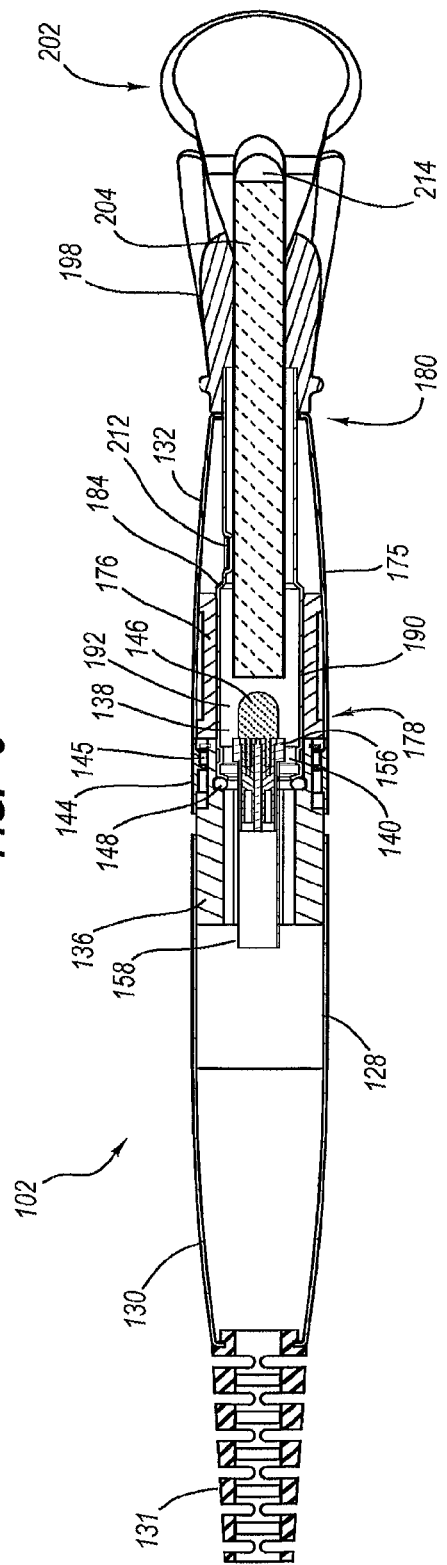

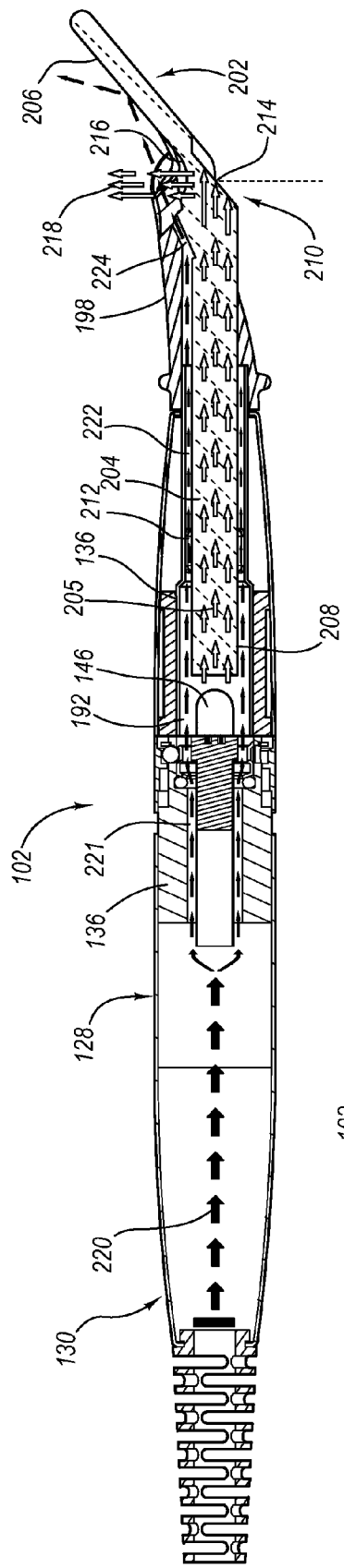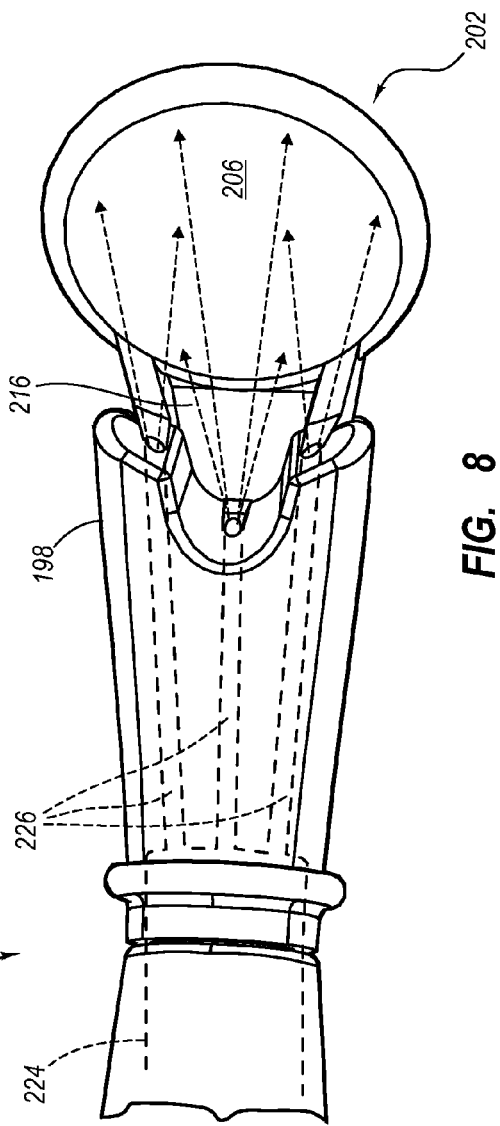

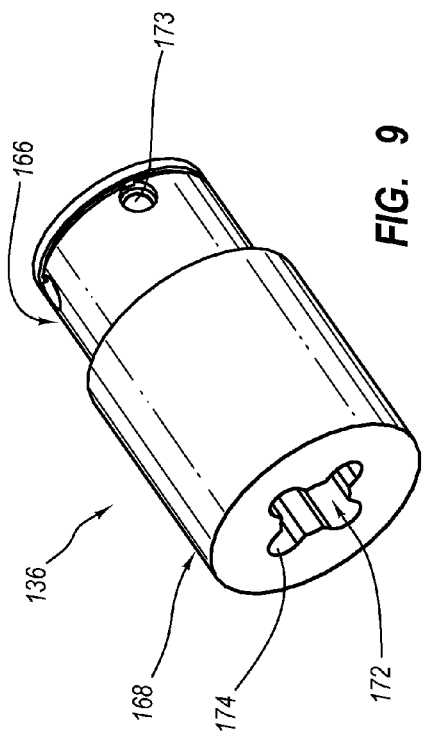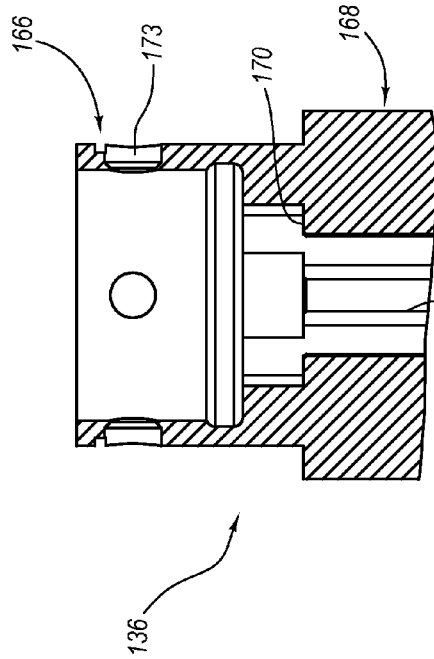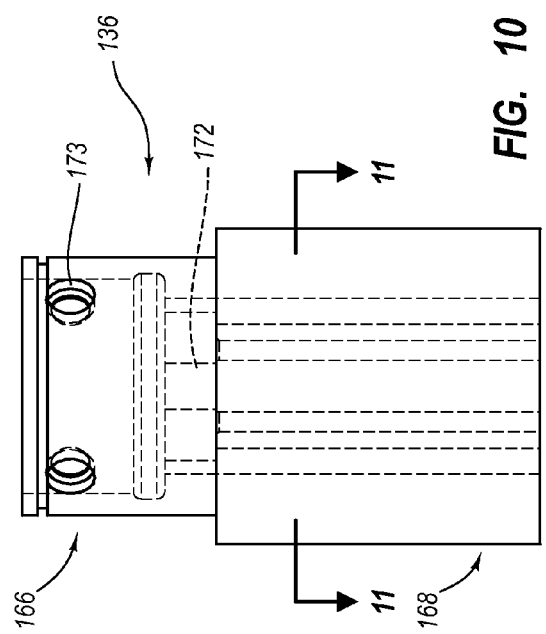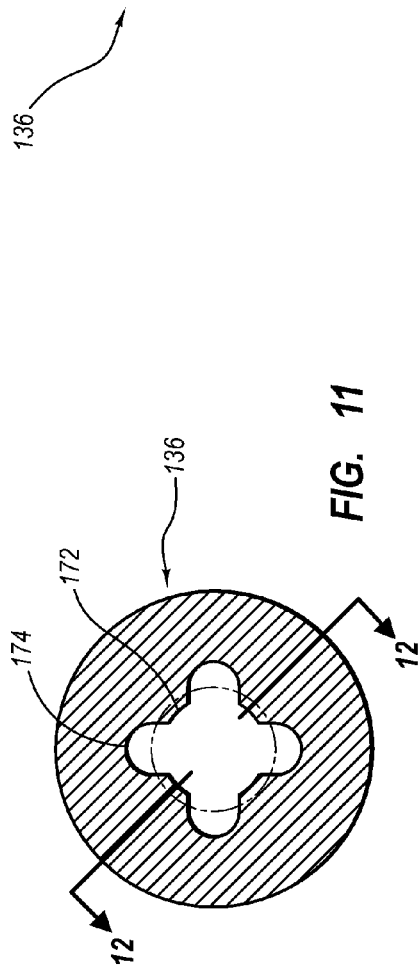

LIGHT MIRROR

TECHNICAL FIELD

The present invention relates generally to hand-held medical instruments, and, more particularly, to hand-held mirrors which may be illuminated by a light source and defogged by a fluid flow.

BACKGROUND

Hand-held medical instruments such as dental mirrors have long been known and used the clinical field of dentistry. Dental mirrors allow clinicians to view various parts of the mouth and throat (if used with an extension) that may be difficult or impossible to see by a direct line of sight. However, some parts of the mouth are difficult to see even with the aid of a dental mirror. The lighting conditions inside of a patient's mouth are often poor, at best. A dark dental mirror is often of limited use. Therefore, over the years, the dental industry has sought to develop a mirror with its own illumination system rather than depending on the light available from an overhead lamp. Examples of such mirrors are disclosed in U.S. Pat. No. 3,638,013 to Keller; U.S. Pat. No. 4,279,594 to Rigutto; U.S. Pat. No. 4,629,425 to Detsch; U.S. Pat. No. 4,993,945 to Kimmelman et al.; U.S. Pat. No. 5,139,420 to Walker; U.S. Pat. No. 5,139,421 to Verderber; U.S. Pat. No. 5,457,611 to Verderber; and U.S. Pat. No. 6,443,729 to Watson (hereby incorporated in its entirety by this reference). The most successful of these mirrors have been those which contain a light source built in the handle of the mirror. The mirror disclosed in U.S. Pat. No. 5,457,611 to Verderber is such a device and is the only known illuminated mirror that has been successfully marketed. The Verderber mirror is marketed by Welch-Allyn, Inc., of Skaneateles, N.Y. However, the Verderber mirror splits a light beam in multiple directions, reducing the intensity of light directed to portions of the mouth of interest. Some have also used unsophisticated penlights whereby a traditional mirror or a disposable plastic mirror is clipped on to the penlight. The penlights, however, are similar to basic flashlights, and the plastic clip-on mirrors have poor optical qualities. Therefore, the results have been less than satisfactory.

One of the problems with illuminated mirrors is the heat generated by the illumination source. Prior illuminated mirror handles heat up to uncomfortable temperatures. As a result, the user (e.g., a dental clinician) may have a tendency to put the mirror down repeatedly during clinical procedures. Also, the clinician may be inclined to alternate mirrors during longer procedures to avoid the discomfort. These practices invariably prolong procedures, distract the clinician, and compromise accuracy, all to the potential detriment of the patient.

One solution to the heat problem is proposed in U.S. Pat. No. 5,457,611 to Verderber. Verderber includes a high intensity lamp contained by a heat sink mounted within the dental mirror handle. The handle contains multiple vents spaced from and surrounding the heat sink. Heat from the lamp attempts to radiate through the vents from the heat sink. The radiating heat may create a thermal current, causing heated air to exhaust through the vents and be replaced by cooler air from the surrounding atmosphere ("ambient cooling"). Even with the aid of ambient cooling, the heat generated by the lamp becomes particularly noticeable within five to ten minutes. Handle temperatures for the Verderber mirror reach 134 degrees F., which is uncomfortable and distracting to the clinician.

Another longstanding shortcoming inherent with conventional dental mirrors is the tendency of the reflective surface to become obscured during clinical procedures. Fog, mist, spray from dental drills, tooth debris, dental materials, etc., collect on the mirror's reflective surface, impairing the visibility of the image reflected by the mirror. The need for clear mirrors in dental and otolaryngology offices continues. Procedures ranging from routine hygiene to extensive oral surgeries can benefit from a clear, illuminated mirror.

Currently, clinicians (or an assistant) must repeatedly clean or wipe the reflective surface, which requires repositioning of the mirror and redirection of the clinician's attention, the assistant's attention, or both. This repeated repositioning and redirection of attention, however, can disrupt the concentration of the clinician, leading to reduced accuracy. In addition, mirror-cleaning takes time, and in many cases a patient will benefit from shorter procedure times. In some cases, clinicians or assistants may attempt to wash the mirror with water, but water distorts the image in the mirror and again redirects the attention of the clinician and/or the assistant from the primary function of controlling the operative field.

Another problem with dental mirrors is the susceptibility of the reflective surface to marring by tooth debris, dental materials, or aluminum oxide powder from air-abrasion systems. When such marring occurs, the mirror must be replaced. Replacement mirrors add to the cost of treating a patient. Water flows can be used to clean and protect (to some degree) the reflective surface from abrasion, but the use of water creates at least two new problems. As mentioned above, water distorts of the image reflected by the mirror, and the water must be removed from the patient's mouth.

One other problem associated with dental mirrors is the risk of transmitting germs from one patient to another (i.e., "cross contamination"). Cross contamination may result from handle exposure to multiple patients. Currently, the recommended approach for preventing cross contamination is an autoclave procedure for the mirror handle after each use. However, this approach is time consuming and requires access to and handling of autoclave equipment and materials. The autoclave process increases the wear-and-tear on the mirror handle. Therefore, many clinicians do not follow the recommended approach.

In addition, traditional dental mirrors are not ergonomic. Ergonomics refers to the ease and precision with which instruments can be positioned for control, direction, duration and distance of applied force. When dental clinicians changed posture in the late 1960s from a standing position to a sitting position, the same dental mirrors remained. The angle of the traditional dental mirror surface to the mirror handle is set at approximately thirty-eight degrees. This angle supplies reflected vision for an operator who stands slightly behind, completely behind, or beside a seated patient. However, the standard thirty-eight degree angle is not designed for clinicians sitting in relation to a patient. Dougherty, Dr. Michael: "Ergonomic Principles in the Dental Setting," DENTAL PRODUCTS REPORT, July 2001, (http://www.dentalproducts.net/xml/display.asp?file=313&bhcp=1).

SUMMARY

The principles described herein may address some of the above-described deficiencies and others. Specifically, some of the principles described herein relate to light devices, light mirrors, and methods of cooling light devices and light mirrors.

One aspect provides a light mirror. In one embodiment, the light mirror comprises a handle having a longitudinal axis, a mirror attached to the handle and arranged at an angle from the longitudinal axis, a light source inside the handle, and a light waveguide adjacent to the light source. In one embodiment, the waveguide comprises a reflector and the reflector reflects substantially all of the light from the light waveguide. In one embodiment, the light waveguide comprises a concave light exit surface for diffusing light from the light source. The concave light exit surface for diffusing light from the light source may be formed in a lateral edge portion of the waveguide. In one embodiment, the light waveguide comprises a first end adjacent to the light source, and a second end. The second end comprises a flat angled reflector aimed at a concave exit surface. In one embodiment, the light waveguide comprises a shank of the mirror. In one embodiment, the light source comprises an LED. In one embodiment, the light mirror further comprises an airflow annulus between the light source and the handle. The airflow annulus between the light source and the handle may provide convection heat transfer from the light source. In one embodiment, the light mirror further comprises an airflow annulus between the light source and the handle, and an elastomeric boot disposed between the mirror and the handle, the elastomeric boot comprising a flow channel in fluid communication with the airflow annulus and aimed at the mirror. In one embodiment, the light mirror further comprises an airflow annulus between the light source and the handle, and an elastomeric boot disposed between the mirror and the handle, the elastomeric boot comprising a plurality of diverging channels in fluid communication with the airflow annulus.

One aspect provides a light mirror apparatus. In one embodiment, the apparatus comprises a handle having a longitudinal axis, a disposable mirror comprising a reflective surface attached to the handle and arranged at an angle from the longitudinal axis, an LED inside the handle, a light waveguide adjacent to the LED, the light waveguide directing light from the LED, an annulus disposed between the LED and the handle and extending between the light waveguide and the handle, and a flow manifold in fluid communication with the annulus, the flow manifold aimed at or across the reflective surface of the mirror. One embodiment further comprises a pressurized air supply coupled to the handle. One embodiment further comprises a roll-up sleeve attached around the handle. In one embodiment, the light waveguide comprises a shank of the disposable mirror. In one embodiment, the light waveguide comprises a first end optically coupled to the LED, and a second end. The second end comprises a reflecting angle aimed to a concave exit surface. In one embodiment, the light waveguide comprises a first end optically coupled to the LED, and a second end, the second end comprising a reflector aimed to a lateral light exit surface, the lateral exit surface comprising a light diffuser. One embodiment further comprises an LED socket, the LED socket comprising, in cross section, an LED receiving hole and a plurality of annular bulbs. In one embodiment, the light waveguide comprises a shank of the disposable mirror, the flow manifold comprises a rubber boot at a distal end of the handle, the shank extends though a hole in the rubber boot, and the rubber boot provides a friction fit with the shank.

One aspect provides an illuminated mirror apparatus. The apparatus comprises a handle having a longitudinal axis, a mirror having a shank, the shank comprising a waveguide having only a single exit surface, the mirror attached to the handle and arranged with a reflective surface at an angle from the longitudinal axis. The apparatus also includes an LED inside the handle, and an internal air passageway substantially parallel to the longitudinal axis and open to the LED. The internal air passageway comprises an annulus between the shank and the handle, the internal air passageway in fluid communication with a manifold directed at the mirror. In one embodiment, the single exit surface comprises a lateral, concave, light diffusing surface directing light centered substantially perpendicular to the longitudinal axis. In one embodiment, the single exit surface is shaped to focus light from the LED on the reflective surface of the mirror.

One aspect provides an illuminated mirror apparatus comprising a handle having a longitudinal axis, a mirror having a shank, the shank comprising a waveguide having a single exit surface, the mirror attached to the handle and arranged with a reflective surface at an angle from the longitudinal axis; a light source inside the handle and optically connected to the waveguide, an internal air passageway substantially parallel to the longitudinal axis and open to the light source, the internal air passageway comprising an annulus between the shank and the handle, the internal air passageway in fluid communication with a flow exit at the reflective surface of the mirror; and a boot attached to the apparatus at a distal end of the handle. The shank extends though a hole in the boot, and the boot provides a supporting friction fit with the shank. In one embodiment the boot comprises a rubber boot, and the rubber boot comprises a manifold between the annulus and the flow exit. In one embodiment the flow exit comprises multi-directional flow paths aimed at the reflective surface of the mirror.

One aspect provides a method comprising providing a medical mirror configured for use in a patient's mouth, illuminating an internal light source of the medical mirror, directing substantially all light from the internal light source through only a single light outlet, cooling the medical mirror with a fluid flow in direct contact with the internal light source, and defogging a reflective surface of the medical mirror with the fluid flow. In one embodiment, the medical mirror comprises a longitudinal axis, and the cooling comprises directing the fluid flow through an annulus inside the medical mirror that is substantially parallel with the longitudinal axis. In one embodiment, directing substantially all light comprises reflecting substantially all light though a light diffuser outlet. In one embodiment, directing substantially all light comprises diffusing substantially all LED light though a concave surface of a light waveguide.

One embodiment provides an illuminated mirror apparatus, comprising an ergonomic handle having a longitudinal axis, a mirror attached to the handle and arranged with a reflective surface at an approximate angle of forty-five degrees with respect to the longitudinal axis, a light source inside the handle, and an air passageway flowing through the handle, the air passageway in fluid communication with a manifold directed at the mirror. In one embodiment, the air passageway is internal to the handle, substantially parallel to the longitudinal axis, and open to the light source. In one embodiment, the internal air passageway comprises an annulus between internal components of the illuminated mirror apparatus and the handle.

One embodiment provides an apparatus comprising an untethered, portable light mirror. The untethered, portable light mirror comprises a handle having a longitudinal axis, a mirror attached to the handle and arranged at an angle from the longitudinal axis, a battery pack providing power to the handle, a light source inside the handle powered by the battery pack, and a light waveguide adjacent to the light source. The waveguide comprises a reflector. In one embodiment, the reflector reflects substantially all of the light from the light waveguide. In one embodiment, the battery pack is attached within the handle. In one embodiment, the battery pack is portable and connected to the handle by a short cord. In one embodiment, the apparatus further comprises a fan powered by the battery pack. In one embodiment, the apparatus further comprises an airflow annulus between the light source and the handle, a fan providing air through the airflow annulus, and an elastomeric boot disposed between the mirror and the handle, the elastomeric boot comprising a flow channel in fluid communication with the airflow annulus and aimed at the mirror. In one embodiment, the untethered portable light mirror may include one or more portable canisters connected to the handle and in fluid communication with an airflow annulus between the light source and the handle. In one embodiment, there is at least one portable compressed air canister in the battery pack.

One embodiment provides an apparatus comprising a trans-illumination light. The trans-illumination light comprises a handle having a longitudinal axis, an LED inside the handle, a longitudinal light waveguide adjacent to the LED and extending from a distal end of the handle, the light waveguide directing light from the LED; an annulus disposed between the LED and the handle and extending between the light waveguide and the handle; and a flow exit from the distal end of the handle.

BRIEF DESCRIPTION OF THE DRAWINGS

The accompanying drawings illustrate certain embodiments discussed below and are a part of the specification.

FIG. 3A is a top plan view of an illuminated mirror showing a protective sheath prior to deployment according to one embodiment.

FIG. 3B is a top plan view of the illuminated mirror of FIG. 3A showing the protective sheath partially deployed according to one embodiment.

FIG. 3C is a top plan view of the illuminated mirror of FIG. 3A showing the protective sheath fully deployed according to one embodiment.

FIG. 4 is a perspective view of the illuminated mirror of FIG. 2, shown with the mirror and associated components detached.

FIG. 5 is a magnified side cross-sectional view, taken along line 5-5 of FIG. 4, of the illuminated mirror according to one embodiment.

FIG. 6 is a magnified cross-sectional view, taken along line 6-6 of FIG. 4 of the illuminated mirror according to one embodiment.

FIG. 7 is a magnified side cross-sectional view, taken along line 5-5 of FIG. 4, showing air flow lines and light passages of the illuminated mirror according to one embodiment.

FIG. 8 is an elastomeric boot manifold according to one embodiment with hidden lines illustrating flow channels.

FIGS. 9-12 illustrate a connector according to one embodiment.

Throughout the drawings, identical reference characters and descriptions indicate similar, but not necessarily identical, elements.

DETAILED DESCRIPTION

Illustrative embodiments and aspects are described below. It will of course be appreciated that in the development of any such actual embodiment, numerous implementation-specific decisions must be made to achieve the developers' specific goals, such as compliance with system-related and business-related constraints, that will vary from one implementation to another. Moreover, it will be appreciated that such a development effort might be complex and time-consuming, but would nevertheless be a routine undertaking for those of ordinary skill in the art having the benefit of this disclosure.

As used throughout the specification and claims, the term "waveguide" refers to a system of material boundaries that may take the form of a solid dielectric rod or dielectric-filled tubular conductor capable of guiding electromagnetic waves. A "bulb" is a radial projection or part that may be rounded. "Convection" means heat transfer by a forced fluid current from one region to another. "Untethered" means not attached by a tether, cord, or umbilical to a relatively unmovable object. The words "including" and "having," as used in the specification, including the claims, have the same meaning as the word "comprising."

Figure 1:
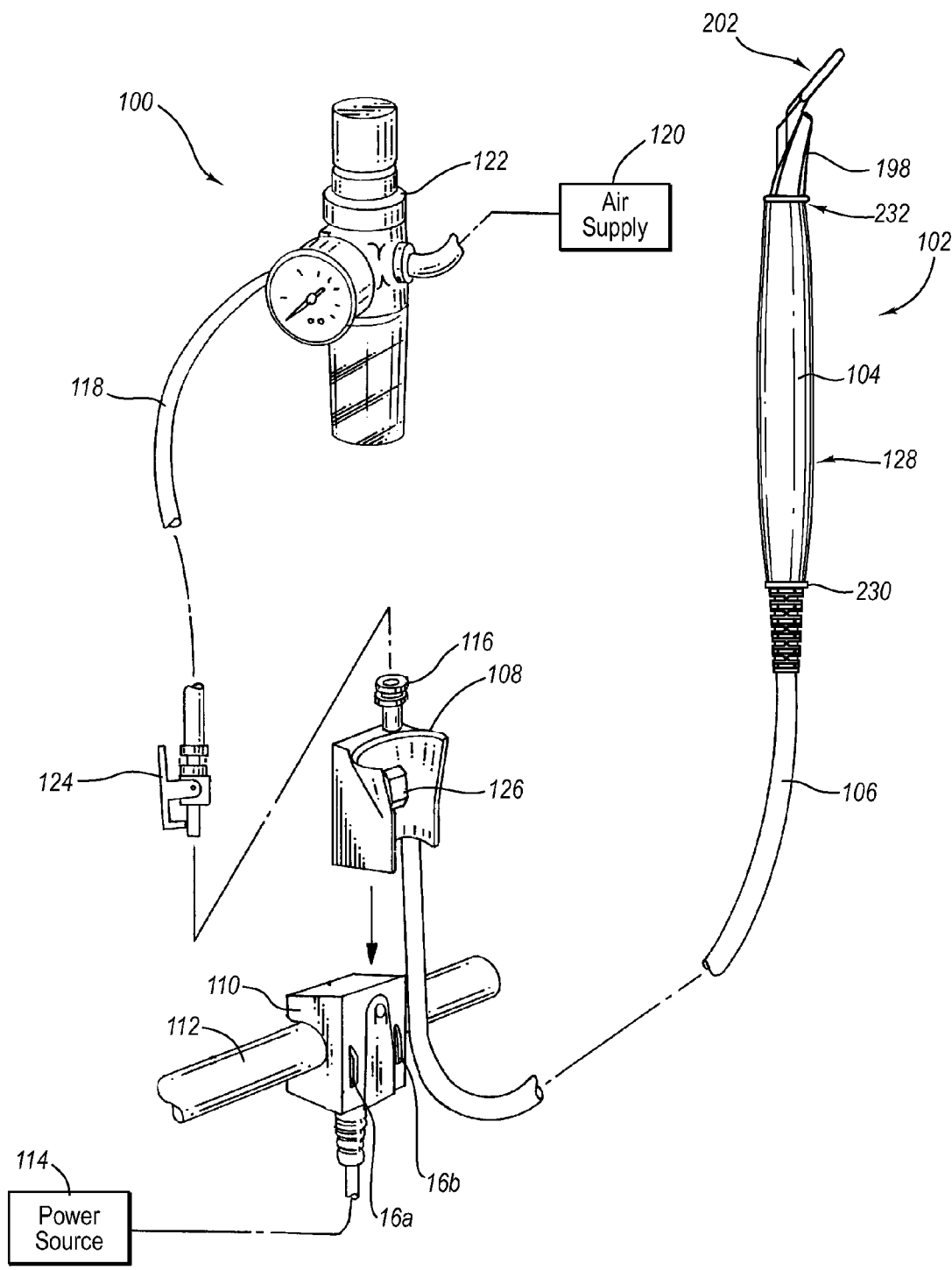
FIG. 1 is a perspective view of an illuminated mirror with associated components, in accordance with one embodiment.

Turning now to the figures, and in particular to FIG. 1, one embodiment of an illuminated mirror system 100 is shown. The illuminated mirror system 100 includes a light mirror 102, which may include an optional protective roll-up sheath 104 covering the instrument. The light mirror 102 is operatively connected to a tether or an umbilical 106. In one embodiment, the umbilical 106 supplies electricity and pressurized air to the light mirror 102. The umbilical 106 may be coupled to an instrument holder 108. The instrument holder 108 is receptive of the light mirror 102.

In one embodiment, the instrument holder 108 is removably secured to a mounting block 110. The mounting block 110 is attached to a support structure 112. An electrical power supply 114 may supply electrical energy to the mounting block 110. The instrument holder 108 and mounting block 110 each contain a pair of electrical contacts. For example, electrical contacts 16a, 16b of the mounting block 110 may be in physical contact with matching contacts (not shown) of the instrument holder 108 when the mounting block 110 and the instrument holder 108 are interconnected. In one embodiment, electrical energy from the power source 114 is transmitted to the light mirror 102 via the mounting block 110, instrument holder 108, and the umbilical 106. The construction and electrical operation of the assembly is well known and fully described in U.S. Pat. No. 5,385,468 to Verderber, which is incorporated herein by reference. However, the light mirror 102 may be connected in any way to any electric and air supply, or may even have on-board supplies. The system 100 illustrated in FIG. 1 is one exemplary embodiment.

In the embodiment of FIG. 1, the instrument holder 108 may include a compressed air fitting 116 connected to and in fluid communication between the umbilical 106 and an air supply line 118. A typical medical or dental office air supply 120 may be coupled to the fitting 116 to provide pressurized air to the light mirror 102. As shown in FIG. 1, in one embodiment, a compressed air filter/regulator 122 is arranged between the air supply 120 and the fitting 116 to remove most liquids and solid particles from the air and regulate air pressure. In one embodiment, air pressurized to about 10-60 PSI is supplied to the umbilical 106. A quick-disconnect connector 124 may be used to connect the air supply 122 to the fitting 116. Air pressure of about 10 PSI may be used to defog the mirror, and higher pressures of about 50-60 PSI may be used during operative procedures to remove debris resulting from the use of high speed instrumentation.

In one embodiment, a manual shutoff valve (not shown) may be included between the filter/regulator 122 and the fitting 116. In one embodiment, the holder includes an automatic shutoff valve. An electrical switch 126 may turn power off and on, and/or open and close an air shutoff valve. The switch 126 is depressed and turns off the electric power to light mirror 102 when the light mirror 102 is placed in the instrument holder 108. Electric power is restored when the light mirror 102 is removed from the instrument holder 108. Likewise, the switch 126 may control the compressed air. In one embodiment, the switch 126 is used with an electrically powered automatic shutoff valve (e.g., a solenoid actuated valve) located in the instrument holder 108 to turn the pressurized air on and off.

Referring next to FIGS. 2-6, structures associated with certain embodiments of the light mirror 102 are shown. In one embodiment, the umbilical 106 is attached to a shell or handle 128 of the light mirror 102. In one embodiment, the handle 128 comprises a tail end 130 having a strain release device. In one embodiment, the strain release device comprises a flexible tail 131. Air and electrical transmission lines pass through the flexible tail 131, and the flexible tail 131 facilitates any orientation of the light mirror 102 with respect to the umbilical 106.

In one embodiment, the handle 128 is ergonomically shaped. Therefore, the handle 128 may comprise a outer diameter and shape or curves conducive to comfortable, long term use. The handle 128 is shaped with contours that minimize hand stress when used by a clinician. Traditional dental mirror handles are very small and can be uncomfortable to use long-term. Some embodiments of the handle 128 described herein have diameters at least twice as large as conventional dental mirrors and are much more comfortable to use. However, some embodiments have diameters similar or identical to traditional dental mirrors.

In one embodiment, the handle 128 is divided into separate components. For example, as shown in FIGS. 3A and 4, the handle 128 is divided into the tail end 130 and the head end 132. The head and tail ends 132, 130 of the handle 128 may be selectively connectable. For example, in one embodiment, the head and tail ends 132, 130 may cooperate to form a quick-disconnect coupler 134. The quick-disconnect coupler 134 is described below.

The quick-disconnect coupler 134 includes a coupling pair such as a socket or female connector 136 in the tail end 130, and a male connector 138 in the head end 132, or vice-versa. The male connector 138 includes an external circumferential 140 groove receptive of one or more balls 142 disposed in the female connector 136. A sleeve 144 around the female connector 136 includes an internal circumferential groove 145 (FIG. 6) housing the one or more balls when the head and tail ends 132, 130 are disconnected as shown in FIG. 4. However, when the head and tail ends 132, 130 are urged together, the sleeve 144 is retracted, the male connector 138 enters the female connector 136, and the one or more balls 142 enter the external circumferential groove 140 of the male connector 138. A seal such as an O-ring 148 may be arranged between the male and female connectors 138, 136 when the head and tail ends 132, 130 are connected as shown in FIGS. 3A, 5, and 6. The sleeve 144 may be biased by a spring clip 150 (FIG. 2) to the position shown in FIG. 5, locking the one or more balls 142 in the external circumferential groove 140. The head and tail ends 132, 130 may be separated by retracting the sleeve 144 to overcome the biasing force of the spring clip 150, releasing the one or more balls 142 from the external circumferential groove 140, and pulling the head and tail ends 132, 130 apart. One of ordinary skill in the art having the benefit of this disclosure will recognize that the quick-disconnect coupler 134 is one of any number of connecting devices that may be used to couple and decouple the head and tail ends 132, 130. Moreover, in some embodiments, the head and tail ends 132, 130 may comprise one unitary structure.

In one embodiment, a light source such as an LED 146 or any other light source (e.g. a halogen light bulb, a fiber optic bundle powered by LED, laser, or halogen bulb, etc.) is securely mounted to the female connector 136. In one embodiment, the LED comprises conductor pins 152 that fit snugly or rigidly in a pair of pin receptacles 154. The pin receptacles 154 are in turn disposed in a receptacle housing 156. In one embodiment, the receptacle housing 156 fits at least partially inside, and may be connected to, a tube such as an LED tube 158. The conductor pins 152 are electrically connected by the pin receptacles 154 or other component to a power supply such as the umbilical 106 (FIG. 1). The receptacle housing 156 may comprise a shank 160 and an oversized head 162. The LED tube 158 is generally cylindrical and sized with an inner diameter smaller than the outer diameter of the shank 160. However, the oversized head 162 is larger than the inner diameter of the LED tube 158 and therefore the oversized head 162 abuts the LED tube 158.

Figure 2:
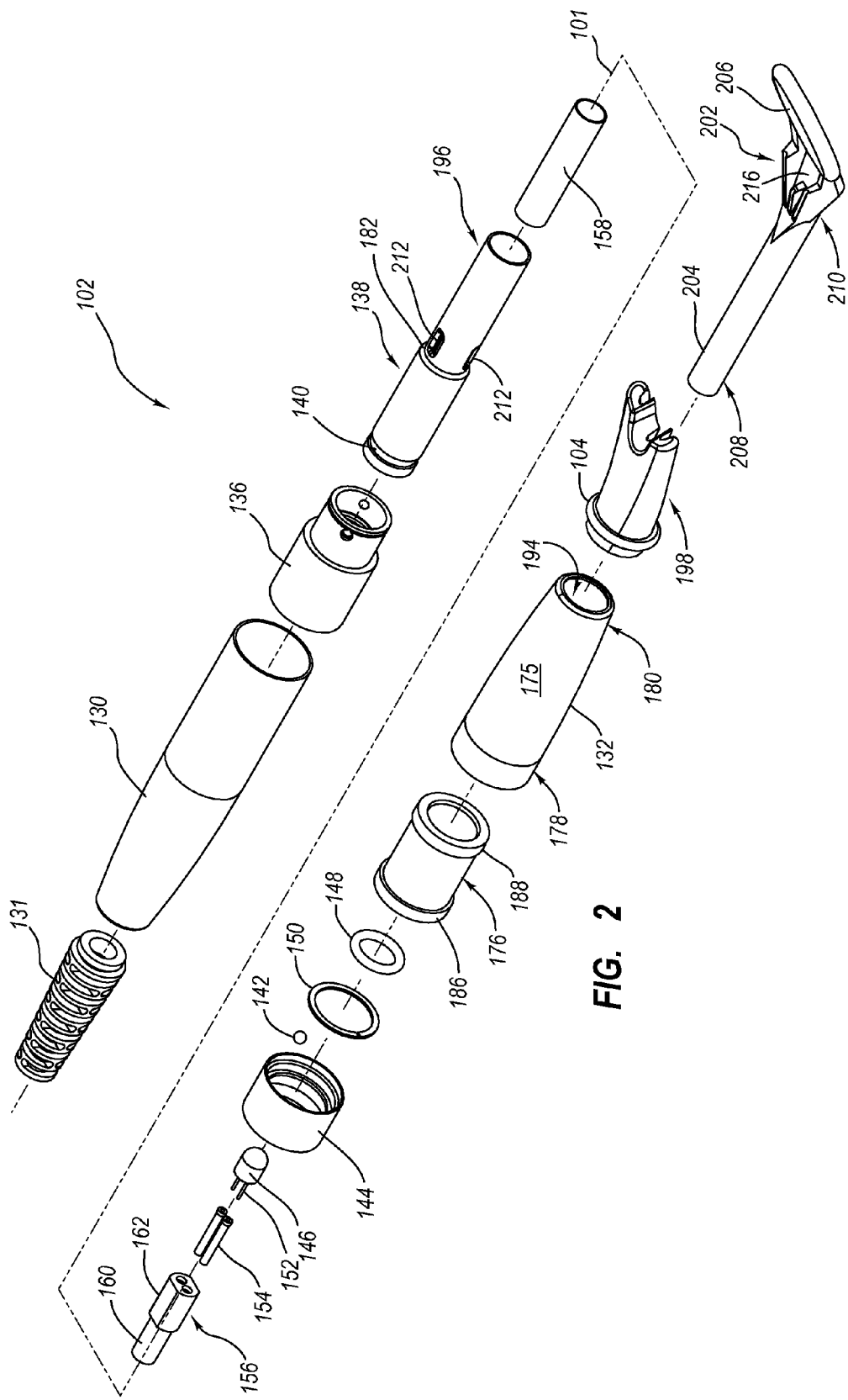
FIG. 2 is an exploded view of an illuminated mirror according to one embodiment.

In one embodiment, the LED tube 158 fits in the female connector 136. As shown in FIGS. 9-12, the female connector 136 may exhibit changing inner and outer diameters. The female connector 136 includes a first end 166 and a second end 168. The inner diameter of the first end 166 receives the male connector 138 (FIG. 3). As shown in FIG. 12, the inner diameter of the first end 166 includes a shoulder 170. The shoulder 170 coincides with a transition to the second end 168. The inner diameter of the second end 168 is smaller than the inner diameter of the first end 166. According to one embodiment, the inner diameters comprise a partially cylindrical passage 172 that is sized to receive the LED tube 158 (FIG. 2). However, the partially cylindrical passage 172 includes one or more bulbs 174 or other projections that extend radially from a cylindrical diameter. In one embodiment, four equally spaced bulbs 174 extend radially from the otherwise cylindrical diameter. The cylindrical diameter securely receives the LED tube 158 (FIG. 2), and the bulbs 174 create an annulus or flow passage between the LED tube and the female connector 136 (FIG. 2).

The first end 166 also includes one or more external recesses 173, for example four recesses 172, that hold the balls 142 (FIG. 5). The first end 166 may comprise an outer diameter that is smaller than the outer diameter of the second end 168. In one embodiment, the sleeve 144 (FIG. 5) fits over the first end 166 and comprises an outer diameter approximately equal to the handle 128 (FIG. 5), such that the sleeve 144 is substantially flush with the handle 128 (FIG. 5).

Referring again to FIGS. 2-6, in one embodiment, the head end 132 comprises a shell 175 that at least partially houses one or more additional components. In one embodiment, the shell 175 is substantially tubular and receptive of a brace or holder 176. The shell 175 is tapered from a first end 178 to a second end 180. Therefore, an internal diameter of the shell 175 decreases from the first end 178 to the second end 180. The shell 175 is also sized to receive a portion of the male connector 138. In one embodiment, the male connector 138 is a substantially tubular member and includes a change in outer diameter. For example, the male connector 138 may include a shoulder 182. The shell 175 may include an internal shoulder 184 sized to bear against the shoulder 182 of the male connector 138 and limit the insertion of the male connector. In one embodiment, the male connector 138 extends from both the first and second ends 178, 180 of the shell 175.

The brace 176 comprises a tubular insert including radial protrusions 186, 188 at both the first and second ends thereof. The radial protrusions 186, 188 are sized to contact an internal diameter of the shell 175 at the first end 178 thereof. The second protrusion 188 may be smaller than the first protrusion 186 to facilitate insertion of the brace 176 into the tapered shell 175. The taper of the shell 175, however, limits insertion of the brace 176. In one embodiment, the brace 176 is inserted until the first radial protrusion 186 is substantially flush with the first end 178 of the shell 175. The brace 176 fits tightly or connects rigidly to the shell 175.

The first radial protrusion 186 comprises an outer diameter substantially matching the diameter of a distal end of the female connector 136. Therefore, the first radial protrusion 186 may abut or interface the distal end of the female connector 136 when the head and tail ends 132, 130 are interconnected as shown in FIGS. 3, 5, and 6.

In one embodiment, the inner diameter of the brace 176 contacts or bears against the outer diameter of the male connector 138. In one embodiment, an interface 190 between the brace 176 and the male connector 138 comprises a tight fit or a glued connection. The inner diameter of the male connector 138 defines an annulus or open space 192 for the LED 146. When the head and tail ends 132, 130 are interconnected as shown in FIGS. 3, 5, and 6, the LED 146 extends into the open space 192.

In one embodiment, the male connector 138 extends through a hole 194 in the second end 180 of the shell 175. A distal end 196 of the male connector 138 extending through the hole 194 receives a manifold, for example an elastomeric boot manifold 198. The elastomeric boot manifold 198 fits rigidly or snugly over the distal end 196 of the male connector 138. The elastomeric boot 198 may include a radial protrusion, which may, for example, provide a convenient gripping surface to a user.

In one embodiment, the elastomeric boot manifold 198 is receptive of a mirror, such as a disposable mirror 202, by a friction fit. The disposable mirror 202 includes a base such as a shank 204 and a head comprising a reflective surface 206. The reflective surface 206 may comprise a generally circular shape. The reflective surface 206 of the disposable mirror 202 is shown at an angle from the shank 204 (and thus at an angle to the longitudinal axis 101 of the light mirror 102). According to some embodiments, the angle between the shank 204 and the reflective surface 206 ranges between approximately twenty and sixty degrees, although any useful angle may be used. In one embodiment, the angle between the shank 204 and the reflective surface 206 is approximately forty-five degrees. A forty-five degree angle has been found to be more conducive to sitting arrangements of a clinician with respect to a patient than prior thirty-eight degree angles. In some embodiments, the angle between the shank 204 and the reflective surface 206 is approximately forty-six degrees or greater.

In one embodiment, the shank 204 comprises a light waveguide or fiber optic shank. The shank 204 may comprise any material conducive to a light waveguide, including, but not limited to, Lexan.® The shank 204 includes a first end 208 and a second end 210. The shank 204 is inserted through the elastomeric boot manifold 198 and into the male connector 138. The male connector 138 may include a plurality of radially inward protrusions or divots 212 that guide and hold the first end 208 of the shank 204 at a substantially central location adjacent to the LED 146. The first end 208 of the shank 204 is optically coupled to the LED 146.

The second end 210 of the shank 204 comprises a reflector 214 and a light exit surface 216. The reflector 214 may comprise an angle formed at the second end 210 of the shank sufficient to reflect all light passing through the shank 204. The reflector 214 may also comprise a polished or mirrored surface. In one embodiment, the reflector 214 comprises a flat angled surface that aims or directs substantially all light passing through the shank 204 to the light exit surface 216. In one embodiment, no or minimal light exits through the reflector 214. According to one embodiment, the light exit surface 216 comprises a lateral, concave surface that diffuses light reflected by the reflector 214. In one embodiment, the concave light exit surface 216 is centered approximately normal or perpendicular to the shank 204 at line 218 (FIG. 7). In one embodiment, the concave light exit surface 216 is aimed toward the reflective surface 206 or centered at another angle relative to the shank 204. An open U-shape of the elastomeric boot manifold 198 may coincide with the lateral, concave light exit surface 216.

Referring to FIG. 7, according to one embodiment, the tail end 130 of the handle 128 is substantially hollow. Moreover, the tail end 130 is open to and in fluid communication with the umbilical 106 (FIG. 1). Therefore, when the light mirror 102 is in operation, pressurized air from the umbilical enters the tail end 130 of the handle 128 as depicted by arrows 220 in FIG. 7. Pressurized air entering the tail end 130 flows through the female connector 136 via the annulus 221 created by the radial bulbs 172 (FIG. 11). The annulus 221 created by the radial bulbs 172 (FIG. 11) is substantially parallel to the longitudinal axis 101 (FIG. 2) of the light mirror 102. The pressurized air flows around and adjacent to the LED 146, effectively cooling the LED 146 primarily by convection heat transfer. The pressurized air is in direct contact with the LED 146 and the handle 128 according to some embodiments. The pressurized air continues through the annulus 192 between the LED 146 and the handle 128 to an annulus 222 created between the shank 204 and the male connector 136. Space between the divots 212 of the male connector 136 allow the pressurized air to continue distally through the handle 128. The annular flow of air through the entire handle 128 and around the LED 146 keep the handle 128 cool and comfortable for clinicians indefinitely.

The annulus 222 is in fluid communication with a main flow channel or path 224 through the elastomeric boot manifold 198. Referring to FIG. 8, in one embodiment, the elastomeric boot manifold 198 comprises a plurality of branches 226 diverging from the main flow path 224. Air streams through the branches 226 toward the reflective surface 206 of the disposable mirror 202. In one embodiment, the branches 226 are aimed at or across the reflective surface 206. Accordingly, air discharges through the branches 226 in a fan-like pattern at or across the reflective surface 206. The air streams through the branches 226 and to the reflective surface 206 clears and/or defogs the reflective surface when the light mirror 102 is in operation in a patient's mouth without the use of water.

When the light mirror 102 is in operation, the LED 146 is energized via the power source 114 (FIG. 1) through the umbilical 106 (FIG. 1). The LED 146 is adjacent to and optically coupled to the shank 204. Therefore, light 205 emitted by the LED 146 is transmitted through the shank 204. In one embodiment, rather than splitting the light from the LED 146 into multiple directions, substantially all of the LED light traverses the shank 204 and is reflected by the reflector 214 at the second end 210 of the shank. The reflector 214 redirects substantially all the light out of the shank 204 through the single light exit surface 216. The light transmitted through the light exit surface 216 illuminates a patient in any direction aimed by the clinician. The reflective surface 206 of the light mirror 102 reflects light from the patient at the illumination areas. Therefore, the light mirror 102 may be used by the clinician to clearly see even the most dark areas of a patient's mouth or other area. Meanwhile, the air passing through the handle 128 keeps the reflective surface 206 clear. In addition, the forced air may also provide a barrier protecting the reflective surface 206 from tooth debris, old dental materials, and the high power water emitting laser technology and aluminum oxide powder from air-abrasion systems. In one embodiment, the light mirror 102 may comprise mostly plastics and elastomers such that the weight of the instrument is about the same as a traditional stainless steel handle and mirror. Further, the larger diameter handle 128 is more ergonomic than the smaller diameter stainless steel handle and mirror. In some embodiments, however, the light mirror 102 may comprise metal such as stainless steel and may be of smaller, more traditional diameter.

As mentioned above, in some embodiments, the light mirror 102 includes the optional protective roll-up sheath 104 (FIG. 1) covering most of the instrument. As shown in FIGS. 1 and 3A-3C, the protective roll-up sheath 104 is a skin that than can be deployed across the light mirror 102 to prevent the spread germs and debris. In one embodiment, the roll-up sheath 104 is an elongated tubular sheath open at both ends. In one embodiment, the roll-up sheath 104 is attached to the elastomeric boot manifold 198. One end 232 of the roll-up sheath 104 is affixed around a perimeter of the elastomeric boot manifold 198. An opposite end 230 (FIGS. 1 and 3C) remains open and free to allow manual deployment over the handle. The roll-up sheath 104 may simply roll up and roll down the handle 128 as desired. FIG. 3A shows the roll-up sheath 104 prior to deployment. FIG. 3B illustrates partial deployment of the roll-up sheath 104 as it is unrolled over the handle 128. FIG. 3C shows the roll-up sheath 104 fully unrolled and covering the handle 128. The roll-up sheath 104 may comprise any flexible, contaminant resistant material including, but not limited to: vinyl, latex, nitrile, and polyethylene. Once deployed as shown in FIGS. 1 and 3C, the roll-up sheath 104 provides a protective, contaminant-resistant barrier over the handle 128, and including the quick-disconnect coupler 134 (FIG. 5). In one embodiment, the mirror 202, elastomeric boot manifold 198, and roll-up sheath 104 are all disposable. Therefore, each of the disposable items may be used a single time and discarded.

Figure 13:
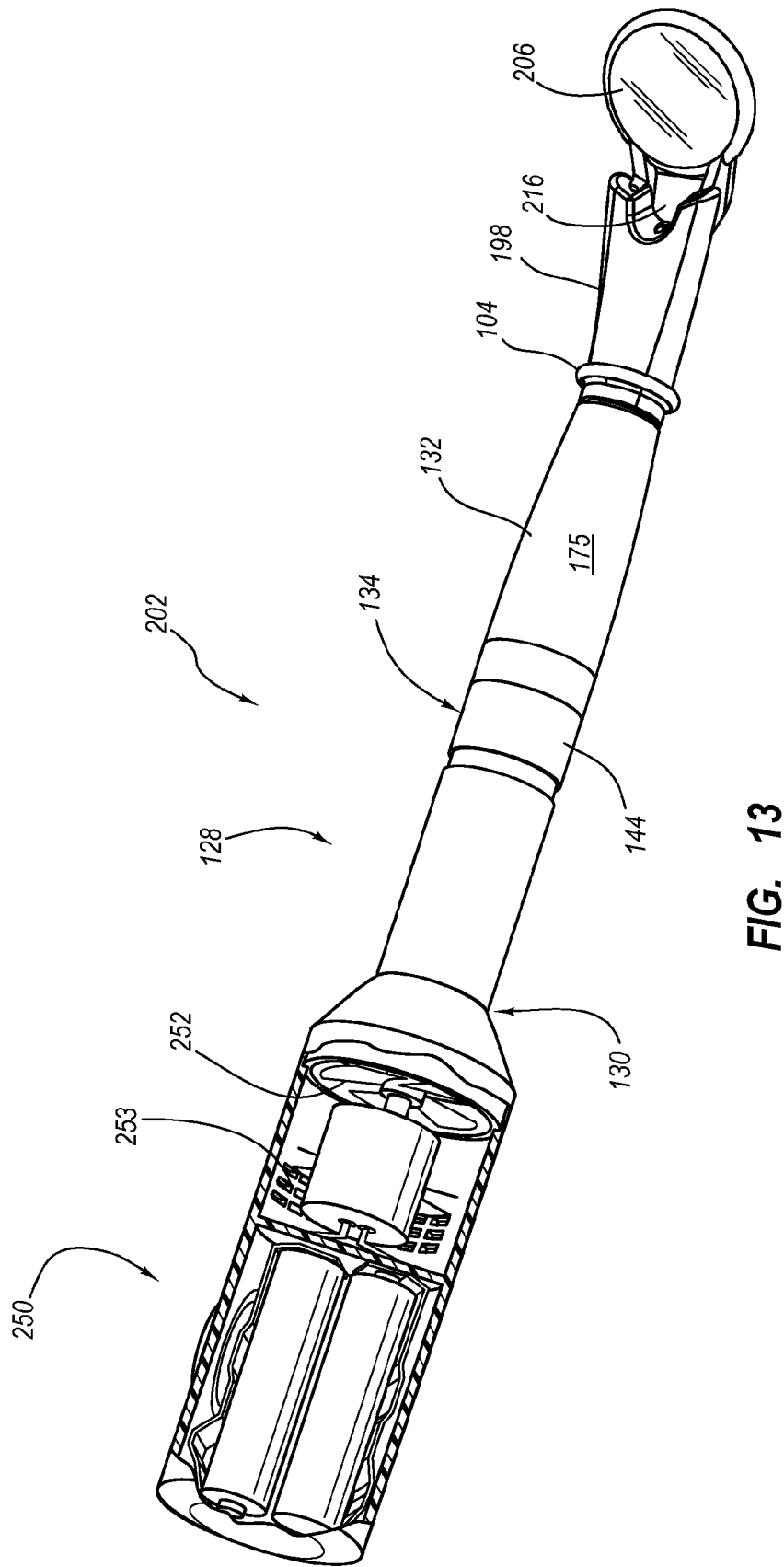
FIG. 13 is a perspective view of an untethered, portable illuminated mirror with a battery pack according to one embodiment.

Referring next to FIG. 13, another embodiment of the light mirror 102 is shown. In the embodiment of FIG. 13, rather than attaching to the umbilical 106 (FIG. 3), the light mirror 102 is untethered and portable. The internal components as described above with reference to FIGS. 2-6 may remain, but there is no umbilical 106 or flexible tail 131. Instead, the light mirror 102 of FIG. 13 includes a battery pack 250. The battery pack 250 is electrically connected to the LED 146 (FIG. 4) and provides power thereto. In some embodiments, the light mirror 102 does not have access to air when it is untethered. However, the battery pack 250 may be removed, and the light mirror 102 may be connected to the umbilical 106 (FIG. 3) when air is needed.

Nevertheless, in some embodiments, the battery pack 250 also supplies power to an optional fan 252. In one embodiment, the fan 252 is enclosed by the battery pack 250 but open by vents 253 to atmosphere. The fan 252 is also in fluid communication with the interior of the tail end 130 of the handle 128. Therefore, air may be forced by the fan 252 into the handle 128 in the same flow path depicted by the arrows 220 of FIG. 7.

Figure 16:
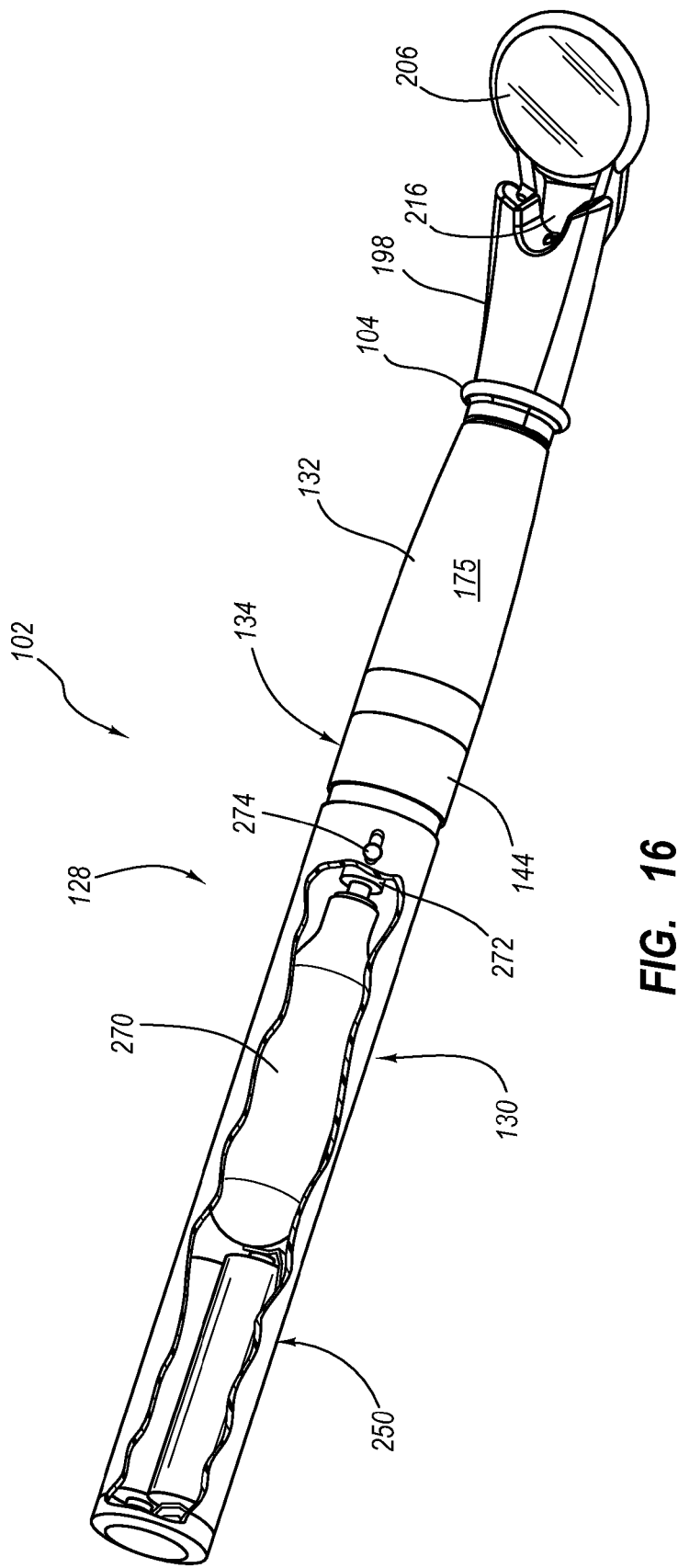
FIG. 16 is a perspective view of an untethered, portable illuminated mirror with a self contained air supply according to one embodiment.

In one embodiment shown in FIG. 16, the light mirror 102 may include one or more compressed air canisters 270 to provide air through the handle 128. The compressed air canister 270 shown in FIG. 16 may replace, or be in addition to, the fan 252 (FIG. 13). The air canister 270 is self contained within the handle 128 or battery pack 250. Like the fan 252 (FIG. 13), the compressed air canister 270 may be in fluid communication with the interior of the tail end 130 of the handle 128. A control valve 272 with a controller 274 may be used by a clinician to turn the air off and on. The air canister 270 may be used with or without embodiments including the battery pack 250. Accordingly, the reflective surface 206 may be kept clean with a portable, stand alone, untethered unit. Moreover, the handle 128 may be kept cool by the flow of air from the air canister 270.

Figure 14:
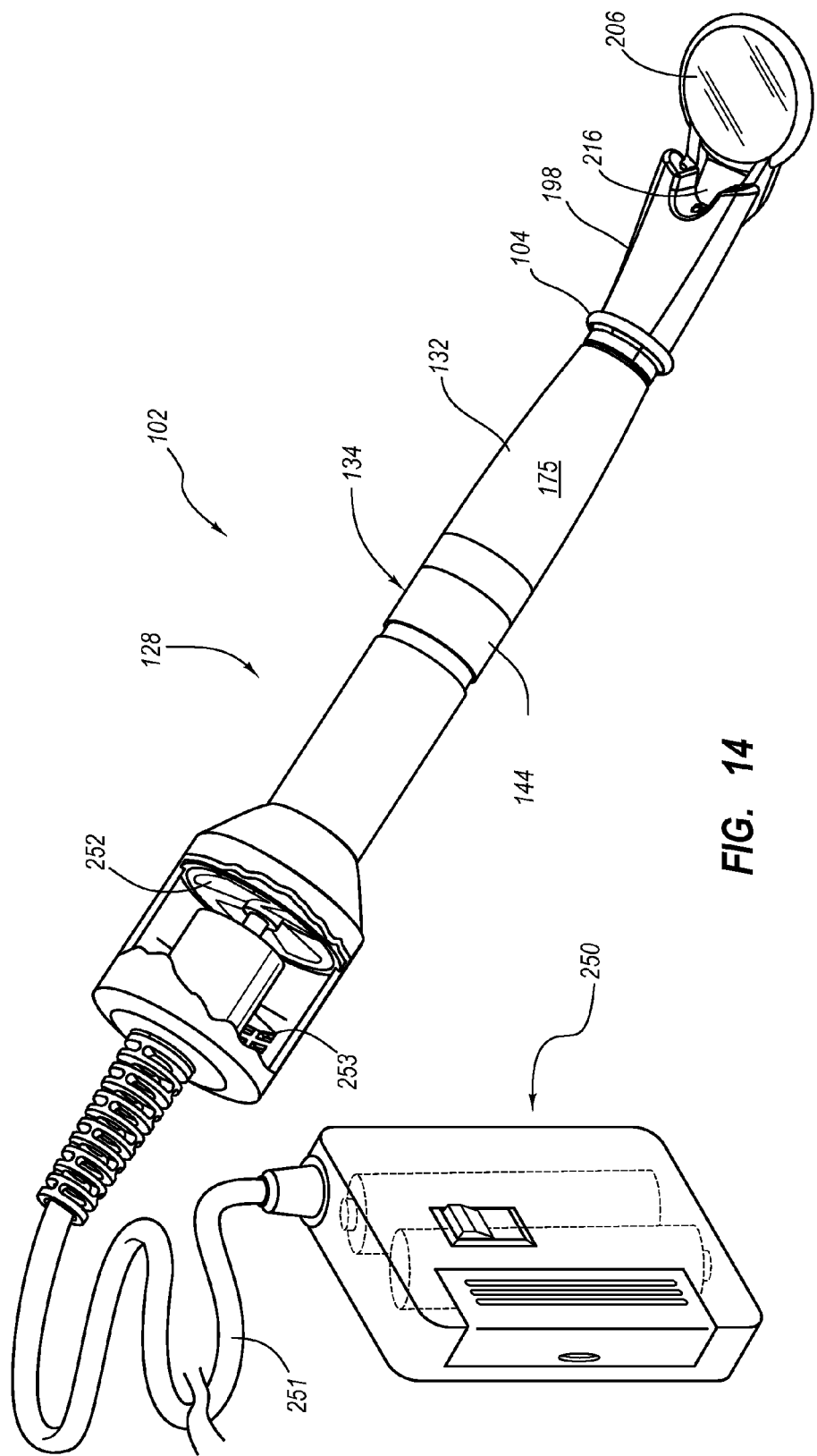
FIG. 14 is a perspective view of an untethered, portable illuminated mirror with a remote battery pack according to one embodiment.

In one embodiment shown in FIG. 14, the battery pack 250 is remote from the handle 128 but still portable and untethered. A short cord 251 may connect the battery pack 250 to the handle 128. The battery pack 250 may clip onto a user's belt, slip into a user's pocket, sit on an object near the handle 128, or otherwise remain in proximity to the handle 128. Accordingly, the battery pack 250 may not add to the weight of the handle 128 and also enable the light mirror 102 to be fully portable. The handle 128 may or may not include the optional fan 252.

Figure 15:
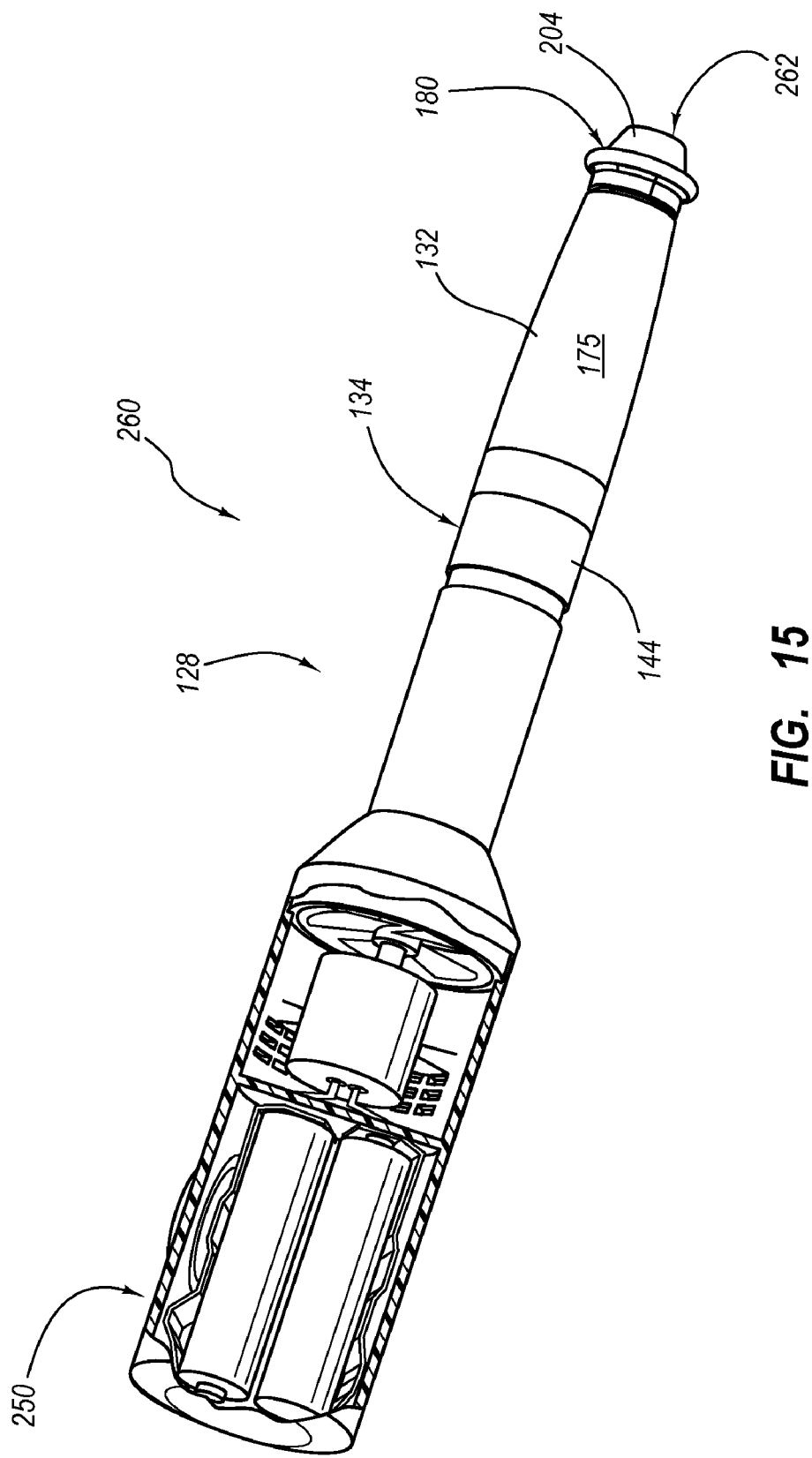
FIG. 15 is a perspective view of a portable, untethered, illuminating rod with a battery pack according to one embodiment.

Another embodiment is shown in FIG. 15. According to the embodiment of FIG. 15, a trans-illumination light 260 is shown. The trans-illumination light 260 may be portable with a battery pack 250 as shown in FIG. 15, or connected to the umbilical 106 (FIG. 3) for power. The internal and external components of the trans-illumination light 260 are similar or identical to light mirror 102 of FIGS. 3 and 13, however, the trans-illumination light 260 does not include the disposable mirror 202 (FIG. 3), and may not include the elastomeric boot manifold 198 (FIG. 3). Instead of a disposable mirror 202, only the shank 204 is inserted into the handle 128. The shank 204 of FIG. 15 does not include the concave light exit surface 216 (FIG. 2). Rather, the shank 204 of FIG. 15 directs all light out through a distal end 262 thereof. Air may optionally continue to flow through the handle 128 as described above in other embodiments to keep the handle 128 and/or the LED 146 (FIG. 4) cool. Air may flow through the elastomeric boot manifold 198 (FIG. 4), or the elastomeric boot manifold may be removed or replaced such that air simply exits the second end 180 around the shank 204. The trans-illumination light 260 may be used in any medical environment to illuminate any area of interest with precision.

The preceding description has been presented only to illustrate and describe certain aspects, embodiments, and examples of the principles claimed below. It is not intended to be exhaustive or to limit the described principles to any precise form disclosed. Many modifications and variations are possible in light of the above teaching. Such modifications are contemplated by the inventor and within the scope of the claims. The scope of the principles described is defined by the following claims. It will be understood that the figures and accompanying text are exemplary in nature, and not limiting.

What is claimed is:

1. A light mirror, comprising:
 a handle having a longitudinal axis;

a mirror attached to the handle and arranged at an angle from the longitudinal axis;
a light source inside the handle;
a light waveguide comprising a shank of the mirror adjacent to the light source;
the light waveguide comprising a first end adjacent the light source and a second end adjacent a reflector, the reflector angled with respect to a longitudinal axis of the light waveguide to direct substantially all of the light to a light waveguide exit;
wherein the reflector and light waveguide exit are adapted to direct substantially all of the light from the light waveguide to a part of the patient in a direction aimed by a clinician.

2. The light mirror according to claim 1 wherein the light waveguide comprises a concave light exit surface for diffusing light from the light source, wherein the diffuse light is adapted to illuminate a larger area of the part of the patient aimed at by the clinician.

3. The light mirror according to claim 1 wherein the reflector comprises a flat angled reflector aimed at a concave exit surface, wherein an angle of the flat angled reflector is adapted to reflect substantially all the light from the waveguide and minimize leak through.

4. The light mirror according to claim 1 wherein the light source comprises an LED.

5. The light mirror according to claim 1, further comprising an airflow annulus between the light source and the handle.

6. The light mirror according to claim 1, further comprising an airflow annulus between the light source and the handle providing convection heat transfer from the light source.

7. The light mirror according to claim 1, further comprising:
an airflow annulus between the light source and the handle;
a boot connectably disposed between the mirror and the handle, the boot comprising a flow channel in fluid communication with the airflow annulus and aimed at the mirror.

8. The light mirror according to claim 1, further comprising:
an airflow annulus between the light source and the handle;
a boot connectably disposed between the mirror and the handle, the boot comprising a plurality of diverging channels in fluid communication with the airflow annulus.

9. A light mirror apparatus, comprising:
a handle having a longitudinal axis;
a disposable mirror comprising a reflective surface attached to the handle and arranged at an angled form the longitudinal axis;
an LED inside the handle;
a light waveguide comprising a shank of the disposable mirror adjacent to the LED, the light waveguide comprising a reflector having an angled surface directing substantially all the light from the LED and adapted to illuminate a part of a patient as directed by a clinician;
an annulus disposed between the LED and the handle and extending between the light waveguide and the handle; a flow manifold in fluid communication with the annulus, the flow manifold aimed at or across the reflective surface of the mirror.

10. The light mirror apparatus according to claim 9, further comprising a pressurized air supply coupled to the handle.

11. The light mirror apparatus according to claim 9, further comprising a roll-up sheath attached around the handle.

12. The light mirror apparatus according to claim 9 wherein the light waveguide comprises a first end optically coupled to the LED, and a second end, the second end comprising the reflector having a reflection angle aimed to a concave exit surface.

13. The light mirror apparatus according to claim 9 wherein the light waveguide comprises a first end optically coupled to the LED, and a second end, the second end comprising the reflector aimed to a light exit surface, the light exit surface comprising a light diffuser.

14. A light mirror apparatus according to claim 9 further comprising an LED socket, the LED socket comprising, in cross section, an LED receiving hole and at least one annular recess.

15. The light mirror apparatus according to claim 9 further comprising an LED socket, the LED socket comprising, in cross section, an LED receiving hole and a plurality of annular bulbs.

16. The light mirror apparatus according to claim 9 wherein:
the flow manifold comprises a boot at a distal end of the handle;
the shank extends through a hole in the boot;
the boot provides a friction fit with the shank.

17. An illuminated mirror apparatus, comprising:
a handle having a longitudinal axis;
a mirror having a shank, the shank comprising a waveguide having an single exit surface and a reflector having an angled surface adapted to direct substantially all light to illuminate a part of a patient as directed by a clinician;
the mirror attached to the handle and arranged with a reflective surface at an angle from the longitudinal axis;
an LED inside the handle;
an internal air passageway substantially parallel to the longitudinal axis and open to the LED, the internal air passageway comprising an annulus between the shank and the handle, the internal air passageway in fluid communication with a manifold directed at the mirror.

18. The illuminated mirror apparatus according to claim 17 wherein the single exit surface comprises a concave, light diffusing surface directing light centered substantially perpendicular to the longitudinal axis.

19. The illuminated mirror apparatus according to claim 17 wherein the single exit surface is shaped to focus light from the LED on the reflective surface of the mirror.

20. An illuminated mirror apparatus, comprising:
a handle having a longitudinal axis;
a mirror having a shank, the shank comprising a waveguide having an exit surface and a reflector angled with respect to a longitudinal axis of the waveguide to direct substantially all the light in a direction aimed by an clinician, the mirror attached to the handle and arranged with a reflective surface at an angle from the longitudinal axis;
a light source inside the handle and optically connected to the waveguide;
an internal air passageway substantially parallel to the longitudinal axis and open to the light source, the internal air passageway comprising an annulus between the shank and the handle, the internal air passageway in fluid communication with a flow exit at the reflective surface of the mirror;
a boot attached to the apparatus at a distal end of the handle;
wherein the shank extends through a hole in the boot;
wherein the boot provides a supporting friction fit with the shank.

21. The illuminated mirror apparatus according to claim 20 wherein the boot comprises a rubber boot, and wherein the rubber boot comprises a manifold between the annulus and the flow exit, the flow exit comprising multi-directional flow paths aimed at the reflective surface of the mirror.

22. A method, comprising;
providing a medical mirror configured for use in a patient's mouth;
illuminating an internal light source of the medical mirror;
directing substantially all light from the internal light source with a waveguide comprising a shank of the medical mirror through only a light outlet adapted to illuminate a part of the patient's mouth by providing a reflective surface angled to direct substantially all the light from the internal light source in a direction aimed by a user; cooling a handle of the medical mirror with a fluid flow in direct contact with the internal light source; defogging a reflective surface of the medical mirror with the fluid flow; and wherein the fluid flow further comprises the step of removing water and debris from the medical mirror thereby keeping the medical mirror clean for an unobstructed view.

23. The method according to claim 22 wherein the medical mirror comprises a longitudinal axis, and wherein the cooling comprises directing the fluid flow through an annulus inside the medical mirror that is substantially parallel with the longitudinal axis.

24. The method according to claim 22 wherein the cooling comprises primarily convection cooling.

25. The method according to claim 22 wherein the directing substantially all light comprises reflecting substantially all light through a light diffuser outlet.

26. The method according to claim 22 wherein the directing substantially all light comprises diffusing substantially all LED light through a concave surface of a light waveguide.

27. An apparatus, comprising:
an untethered, portable light mirror, the untethered, portable light mirror comprising:
a handle having a longitudinal axis;
a mirror attached to the handle and arranged at an angle from the longitudinal axis;
a battery pack providing power to the handle;
a light source inside the handle powered by the battery pack;
a light waveguide adjacent to the light source;
the light waveguide comprising a shank of the mirror having a first end adjacent to the light source and a second end adjacent to a reflector that is angled with respect to a longitudinal axis of the light waveguide to direct substantially all of the light to a light waveguide exit;
wherein the reflector is adapted to direct substantially all of the light from the light waveguide to a part of the patient in a direction aimed by the clinician.

28. The apparatus according to claim 27 wherein the battery pack is attached within the handle.

29. The apparatus according to claim 27 wherein the battery pack is portable and connected to the handle by a cord.

30. The apparatus according to claim 27 further comprising a fan powered by the battery pack.

31. The apparatus according to claim 27, further comprising:
an airflow annulus between the light source and the handle;
a fan providing air through the airflow annulus;
a boot disposed between the mirror and the handle, the elastomeric boot comprising a flow channel in fluid communication with the airflow annulus and aimed at the mirror.

32. The apparatus according to claim 27, further comprising a portable air canister connected to the handle and in fluid communication with an airflow annulus between the light source and the handle.

33. The apparatus according to claim 27 further comprising at least one portable compressed air canister in the battery pack.

34. An apparatus, comprising;
a trans-illumination light, the trans-illumination light comprising:
a handle having a longitudinal axis;
a mirror connected to the handle;
an LED inside the handle;
a longitudinal light waveguide adjacent to the LED and extending from a distal end of the handle, the light waveguide comprising an angled reflective surface directing substantially all the light from the LED to a part of a patient as selected by a clinician;
an annulus disposed between the LED and the handle and extending between the light waveguide and the handle;
a flow exit from the distal end of the handle.

* * * * *